United States Patent [19]

Hoyt et al.

[11] Patent Number: 5,529,243
[45] Date of Patent: Jun. 25, 1996

[54] SCENT DISPENSER

[75] Inventors: Earl Hoyt, Woodstock, N.Y.; Wesley M. Buckner, Hilton Head Island, S.C.

[73] Assignee: Product Innovation Resource, Inc., Hilton Head Island, S.C.

[21] Appl. No.: 371,285

[22] Filed: Jan. 11, 1995

[51] Int. Cl.$^6$ .................................................. A61L 9/04
[52] U.S. Cl. ............................................ 239/56; 239/57
[58] Field of Search .................... 383/35; 229/125.02; 239/53–57

[56] References Cited

U.S. PATENT DOCUMENTS

| | | | |
|---|---|---|---|
| 2,720,419 | 10/1955 | Eby | 239/55 X |
| 2,757,957 | 8/1956 | Samann | 239/53 |
| 3,366,312 | 1/1968 | Lowenberg et al. | 239/125.02 X |
| 3,815,828 | 6/1974 | Engel | 239/56 |
| 4,208,012 | 6/1980 | Dutcher | 239/57 |
| 4,280,649 | 7/1981 | Montealegre | 239/57 X |
| 4,283,011 | 8/1981 | Spector | 239/57 X |
| 4,848,929 | 7/1989 | Rawl | 239/55 X |

FOREIGN PATENT DOCUMENTS

| 765280 | 8/1971 | Belgium | 239/57 |
|---|---|---|---|

*Primary Examiner*—Kevin P. Weldon
*Attorney, Agent, or Firm*—Willard M. Hanger

[57] ABSTRACT

A scent dispensing device comprising a scent impregnated pad of which the side edges are supportingly engaged by the inner side surfaces of a perforated hollow tubular body within which the pad is enclosed. The tubular body is expandable between: (1) a flat-folded, collapsed condition in which a pair of opposing tube wall panels with spaced apart apertures are joined together along their opposite side edges and (2) a dilated condition in which the opposing wall panels bow outwardly of each other creating a tubular body of lenticular cross section of lesser dimension between the wall panel joined side edges than in the flat-folded, collapsed condition. Convex contoured end closure flap members connected to extend across the width of each opposing wall panel at their ends are displaceable inwardly of the opposing wall panels to close the tubular body and establish the dilated condition. The width of the impregnated pad is substantially that of the lenticular lesser cross sectional dimension. Expansion of the flat-folded, collapsed tubular body into the dilated condition with an impregnated pad positioned between opposing wall panels brings the inner portions of the joined wall panel side edges into supporting relationship with the side edges of the impregnated pad.

18 Claims, 2 Drawing Sheets

SCENT DISPENSER

BACKGROUND OF THE INVENTION

The present invention relates to the field of devices for retaining aromatic impregnated material and dispensing the aromatic odors therefrom into the surrounding environment.

Devices of various configurations are well known that serve the function of releasing over a period of time air freshener, perfume scented, deodorizing vapors and the like. In these devices, a mass of absorbent material impregnated with the odor releasing substance, commonly a pad, is contained in the dispenser device from which odors vaporized from the impregnated material are released through apertures in the walls of the device. A special type of odor dispensing device has become popular in recent years in the form of souvenirs or postcards that release a fragrance or scent that is associated with the visual aspects of the souvenir or postcard. Typical of these known scent dispensing devices are those described in U.S. Pat. Nos. 3,964,684; 5,148,983 and 5,304,358.

As is evident from these patents, the internal structural arrangements of previously known scent or odor dispensing devices adequate to retain the scent impregnated mass or pad within the dispenser cavity sufficiently separated from the exterior walls of the dispenser as allows the scented vapor from the impregnated pad to pass through passages between the pad supporting structure for escape through holes in the dispenser are relatively complex and expensive to produce.

SUMMARY OF THE INVENTION

The object of the invention is to produce a scent dispensing device having perforated walls defining an internal cavity within which a scent impregnated pad is secured by minimal structure for exposing a maximum area of the impregnated pad as permits the scented vapors from the pad to escape through apertures in the dispenser.

Another object of the invention is to produce a scent dispensing device into which a scented pad can be installed with minimal effort.

Yet a further object of the invention is to produce a scent dispensing device of minimal cost.

Still another object of the invention is to produce a scent dispensing device of the nature of a souvenir or postcard carrying a graphic indicia and from which a scent relating to the graphic indicia is released.

These objects are achieved by the subsequently described scent dispenser invention combination of: (1) a hollow tubular body that is expandable between a flat, collapsed condition and a dilated condition having a lenticular cross section of lesser internal cross sectional dimension than that of the tubular body in its collapsed condition and (2) a scent impregnated pad having a width substantially that of the lesser cross sectional dimension of the dilated tubular body. The tubular body comprises opposing pairs of perforated wall panels joined together along the length of their side edges such that the wall panels can be flexed to bow outwardly in opposite directions as creates a tubular lenticular cross section and tube end closure flap member protruding beyond and hingedly connected across the width of the wall panels beyond the ends of the respective side edges of the panels. The outer edge of each flap member is convex and the inward displacement of the flap member about their hinge connections with associated wall panels at each end of the collapsed tubular body brings the outer convex edges of the flap members into contact with the opposite wall panel, thereby causing the wall panels to flex outwardly in forming the lenticular shape of the dilated tubular body and close the tubular body ends. The side edges of the narrower width scent impregnated pad placed within the tubular body when in the collapsed condition become engaged by the opposite internal side edge portions of the joined wall panels when flexed outwardly of each other by the inward displacement of the flap member in establishing the tubular body in its dilated condition, thereby retaining the impregnated pad within the closed tubular body with substantially the entire surface of the pad exposed within the cavity from which the scent vapors from the pad pass through perforations in the tubular body wall panels.

DESCRIPTION OF A PREFERRED EMBODIMENT

Figure 2:
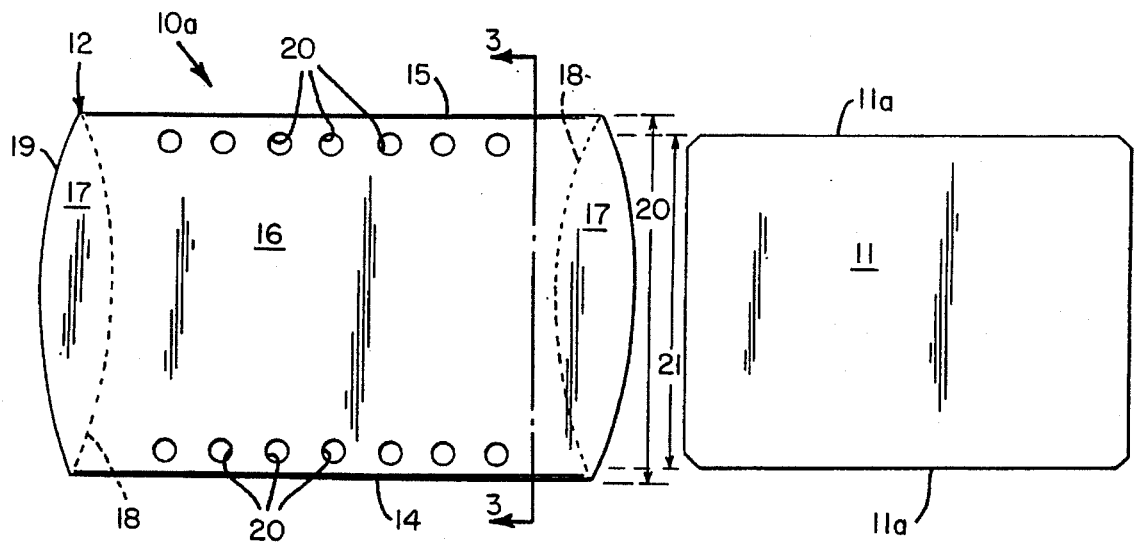
FIG. 2 is a plan view of the components of the present invention comprising the tubular body in its flat-folded, collapsed condition and the scent impregnated pad.
Figure 4:
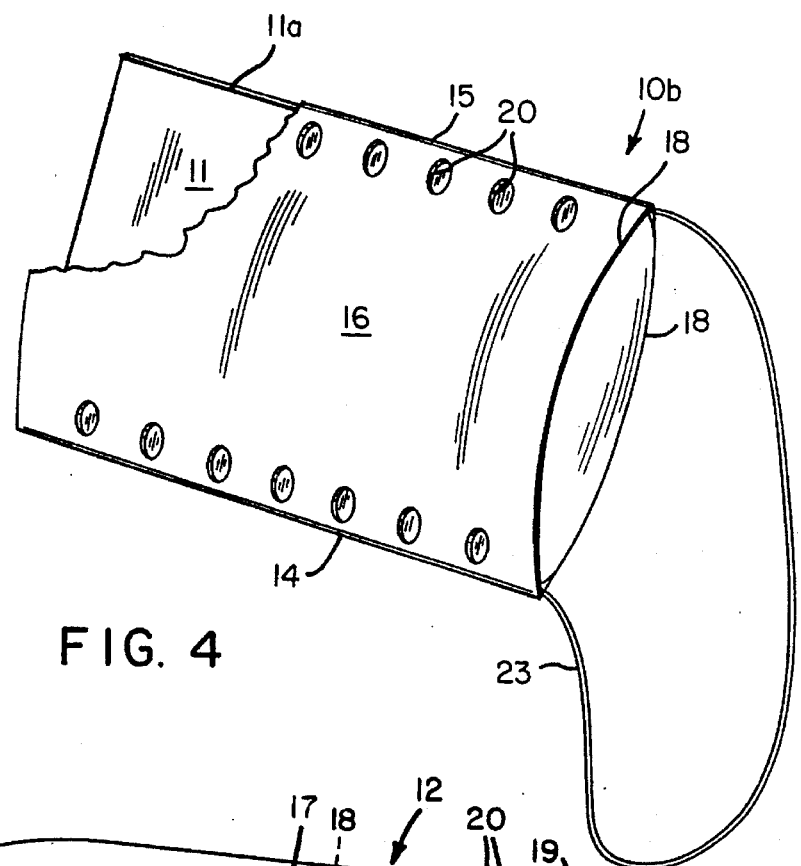
FIG. 4 is a perspective view similar to FIG. 1 with a portion of the tubular body cut away.

First referring to FIGS. 2 and 4, a preferred embodiment of the present invention comprises the combination of the two components of: (1) a tubular body 10 that is expandable between the flat-folded, collapsed condition 10a of FIG. 2 and the dilated condition having a lenticular cross sectional shape of FIG. 4 and (2) a flat, scent impregnated pad 11 insertable into the flat-folded, collapsed tubular body 10a.

Figure 3:
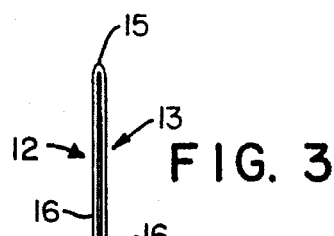
FIG. 3 is a cross sectional view across section line 3—3 of FIG. 2.

Referring to FIGS. 2, 3 and 4, the flat-folded, collapsed tubular body 10a comprises a pair of overlying elongated body forming sections 12, 13 joined together along their respective side edges 14, 15. Each body forming section 12, 13 comprises a centrally located wall panel 16 at each end of which an integral end closure flap member 17 extends the width of the wall panel to protrude beyond the respective ends of the wall panel side edges 14, 15 with a convex-shaped hinge establishing fold line 18 defining the boundary between the wall panel 16 and the integral closure flap member 17. The outer edge 19 of the protruding portion of each flap member 17 is contoured to conform to the convexity of the lenticular cross sectional shape assumed by the tubular body in its dilated condition 10b. The convexity of the hinge fold line 18 is opposite that and of the same convexity as that of the flap member outer edge 19. Each wall panel 16 of the pair of body forming sections 12, 13 is pierced by a series of apertures 20, preferably spaced along the wall panel length adjacent the respective side edges 14, 15 of the panel.

The annular configuration of the overlying body forming sections 12, 13, illustrated in FIGS. 2 and 3, could be conveniently produced from a flat blank comprising juxtaposed body forming sections by folding the blank along a center line between the individual body forming sections as places the body forming sections in an opposing and overlying relationship and securing together the outermost unattached edges of the folded blank by suitable means, such as an adhesive between the inner surfaces of the unattached blank edges or by providing a securing flap extending along an outer edge of one of the body forming sections of the blank and folding the securing flap over and securing it to the other body forming section of the blank after folding the blank.

Figure 1:
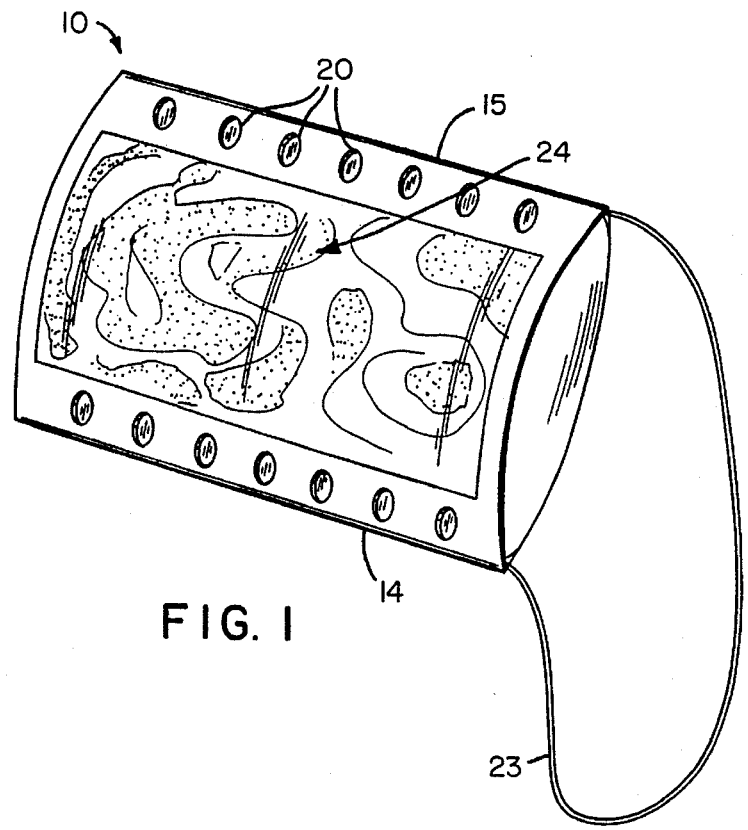
FIG. 1 is a perspective view showing the top and one end of the assembled scent dispenser of the present invention.
Figure 5:
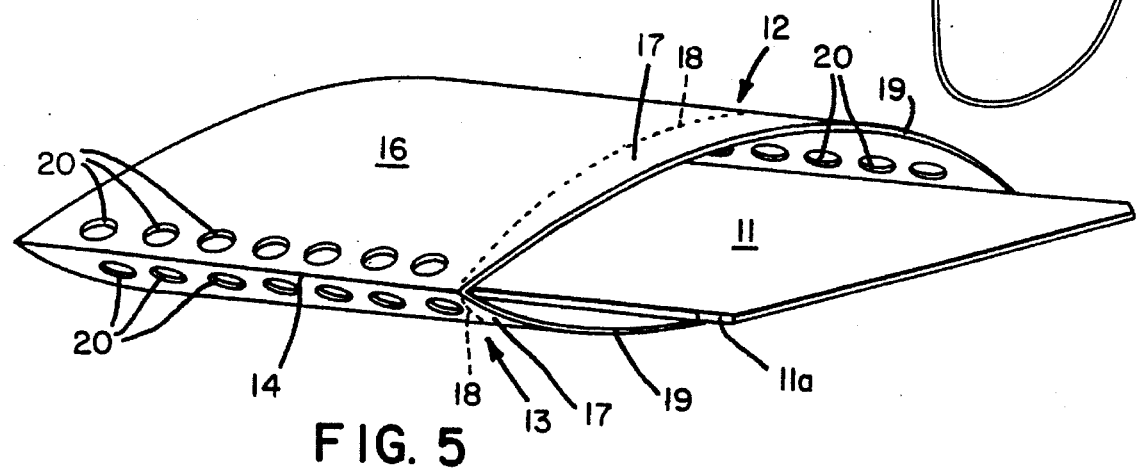
FIG. 5 is a perspective end view of the scent dispenser in a partially assembled condition.

As best seen in FIG. 5, inward pressure exerted against the joined side edges 14, 15 of the body forming sections 12, 13 of the flat-folded and collapsed tubular body 10a flexes the body forming sections 12, 13 outwardly of each other as expands the flat-folded tubular body into a dilated condition of lenticular cross section in which a lesser separation exists between the side edges 14, 15 of the tubular body forming sections 12, 13 than when the tubular body is in its collapsed condition. Folding the end enclosure flap member 17 at each end of the respective wall panel 16 inwardly along the respective hinge fold lines 18 brings the contoured outer edges 19 of the respective flap members 17 into contact with the inner surface of the opposite wall panel 16, thereby establishing the tubular body into a fully dilated condition 10b and closing both ends of the dilated tubular body 10b as illustrated in FIGS. 1 and 4.

The width dimension 21 between the side edges 11a of the scented pad 11 is substantially that of the separation between the interior of the respective wall panel side edges 14, 15 of the fully dilated tubular body 10b of FIG. 4. As illustrated in FIG. 2, the scent impregnated pad 11 width dimension 21 is less than that of the internal cross sectional dimension 22 of the flat-folded, collapsed tubular body 10a so that the pad 11 can be inserted into the interior of the tubular body when in its collapsed or partially deflated condition, as illustrated in FIG. 5.

Assembly of the scent dispenser of the invention is achieved by inserting the scent impregnated pad 11 into the interior of the tubular body to lie in the space defined between the opposing wall panels 16 with the tubular body in the collapsed or partially dilated condition, after which the end enclosure flap members 17 at each end of the respective wall panels 16 are folded inwardly along the respective hinge fold lines 18 as brings the contoured outer edges 19 of the flap members 17 into contact with the inner surface of a flexed, oppositely located wall panel 16. This action in closing the ends of the tubular body and establishing it in its dilated condition decreases the separation between the joined side edges 14, 15 of the overlying panel members 16 along the interior of the dilated tubular body such that the interior portions of the respective panel members 16 extending along their respective joined side edges 14, 15 are brought into an engaging relationship with the opposite side edges 11a of the scent impregnated pad 11, as best seen in FIG. 4. As a convenience in supporting the scent dispenser the ends of a line 23 can be attached to opposite sides of portions of the body forming sections 12, 13. A pictorial or ornamental design or other type of graphic indicia 24 conveniently can be placed on the outer surface of one or both wall panels 16 in creating a souvenir or postcard article and in which the scent with which the pad is impregnated can be related to the graphic indicia. As is clearly illustrated in FIGS. 4 and 5, the scent impregnated pad 11 of the assembled scent dispenser is securely retained along its opposite edges 11a within the closed and dilated tubular body 10b such that substantially all of both surfaces of the impregnated pad 11 are exposed within the closed cavity defined by the fully deflated tubular body 10b such that scent vapors released from the impregnated pad fill the tubular body interior and pass through the apertures 20.

It should be understood that the foregoing disclosure describes a typical embodiment of the invention and that numerous modifications or alterations may be made therein without departing from the spirit and scope of the invention as set forth in the appendant claims.

What is claimed is:

1. A scent dispenser comprising in combination:
   an expandable tubular body adapted for expansion between a flat, collapsed condition and a dilated condition of lenticular cross section having a lesser internal cross sectional dimension than that of the tubular body in said flat-folded, collapsed condition and
   a scent impregnated pad having a width dimension substantially that of said dilated tubular body lesser cross sectional dimension,
   said tubular body comprising:
      an opposing pair of wall panels joined together along their respective opposite side edges in defining a flat-folded tubular body adapted to be dilated by flexing said tubular body wall panels outwardly in opposite directions to form a hollow tubular body of lenticular cross section,
      at least one of said wall panels being pierced by a plurality of spaced apart apertures,
      and tube end closures comprising a flap member hingedly connected across the width of each said wall panel between the ends of the respective side edges of said wall panel and adapted for folding displacement along said hinge connection inwardly of the wall panel to which connected as brings an outer edge of said flap member into contact with an inner surface of an opposite wall panel,
      whereby inward displacement of said flap members closes and establishes said tubular body in said dilated condition such that the opposite side edges of said scent impregnated pad placed within said tubular body prior to expansion come into a supporting relationship with the respective joined side edge portions of said panel members interiorly of said dilated tubular body for retention therewithin.

2. The scent dispenser of claim 1 wherein a flap member is hingedly connected across the respective ends of each said wall panel.

3. The scent dispenser of claim 1 wherein said flap member outer edges have a convex contour shape conforming to that of said tubular lenticular cross section.

4. The scent dispenser of claim 3 wherein said hinge connection comprises a convex fold line extending laterally of said wall panel between the ends of the respective side edges of said wall panel and in which the convexity of said fold line is in a direction opposite that of said flap member outer edge.

5. The scent dispenser of claim 1 wherein each said wall panel has a plurality of apertures spaced apart adjacent each panel side edge.

6. The scent dispenser of claim 1 wherein a graphic indicia is imposed on the exterior face of a wall panel.

7. The scent dispenser of claim 6 wherein the scent of said impregnated pad is associated with the subject matter of said graphic indicia.

8. The scent dispenser of claim 1 wherein the ends of a supporting line are attached to an end of said tubular body.

9. The scent dispenser of claim 7 wherein said supporting line are attached to an end of said tubular body on opposite sides thereof.

10. A scent dispenser comprising a scent impregnated pad supportingly retained within the interior of an expandable, hollow tubular body having a lenticular cross section with side edges of said pad in supporting contact with opposite interior side edge surfaces of said lenticular tubular body, wherein said expandable hollow tubular body comprises:

an opposing pair of wall panels containing spaced apart perforations and joined together along their respective opposite side edges with a tube end closure flap member hingedly connected across the width of each said wall panel between the ends of the respective side edges of said wall panel adapted for folding displacement along said hinge connection inwardly of the wall panel to which connected in defining a flat-folded tubular body adapted for expansion to said lenticular cross sectional tubular body having a lesser internal cross sectional dimension than that of said flat-folded tubular body, said impregnated pad having a width dimension substantially that of said lenticular body lesser interior cross sectional dimension, whereby inward displacement of said flap members along their respective hinge connections flexes said wall panels outwardly of each other to expand said flat-folded tubular body into said lenticular cross section such that opposite side edges of said scent impregnated pad placed within said flat-folded tubular body prior to expansion come into supporting contact with the respective joined side edge portions of said panel members within the interior of said expanded tubular body.

11. The scent dispenser of claim 10 wherein said flap members have an outer free edge having a convex contour conforming to that of said tubular lenticular cross section.

12. The scent dispenser of claim 11 wherein said hinge connection comprises a convex fold line extending laterally of said wall panel between the ends of the respective side edges of said wall panel and in which the convexity of said fold line is in a direction opposite that of said flap member outer edge.

13. The scent dispenser of claim 12 wherein a flap member is hingedly connected across the respective ends of each said wall panel.

14. The scent dispenser of claim 10 wherein each said wall panel has a plurality of apertures spaced apart adjacent each panel side edge.

15. The scent dispenser of claim 10 wherein a graphic indicia is imposed on the exterior face of a wall panel.

16. The scent dispenser of claim 15 wherein the scent of said impregnated pad is associated with the subject matter of said graphic indicia.

17. The scent dispenser of claim 10 wherein supporting means is attached to an end of said hollow tubular body.

18. The scent dispenser of claim 10 wherein said supporting means comprises a line having each end connected to said wall panels at the respective panel side edges.

\* \* \* \* \*